United States Patent [19]

Mori et al.

[11] 4,315,029
[45] Feb. 9, 1982

[54] RACEMIC MODIFICATION CONSISTING OF SPECIFIC ISOMERS OF α-CYANO-3-PHENOXYBENZYL CIS- OR TRANS-2,2-DIMETHYL-3-(2,2,2-TRI-CHLOROETHYL)CYCLOPROPANECARBOXYLATE, PRODUCTION THEREOF AND PESTICIDAL COMPOSITIONS CONTAINING THE SAME

[75] Inventors: Fumio Mori, Kurashiki; Yoshiaki Omura, Mitsu; Yoshiji Fujita, Kurashiki; Takashi Nishida, Kurashiki; Takeo Hosogai, Kurashiki; Fumio Wada, Fukuoka; Sukeji Aihara, Kurashiki; Yoshin Tamai, Kitakanbara; Kazuo Itoi, Kurashiki, all of Japan

[73] Assignee: Kuraray Co., Ltd., Kurashiki, Japan

[21] Appl. No.: 128,717

[22] Filed: Mar. 10, 1980

[30] Foreign Application Priority Data

Mar. 8, 1979 [JP] Japan .................................. 54-27282
Apr. 25, 1979 [JP] Japan .................................. 54-51677

[51] Int. Cl.$^3$ ..................... A01N 53/00; C07C 121/75
[52] U.S. Cl. ................................. 424/304; 260/465 D
[58] Field of Search .................... 260/465 D; 424/304

[56] References Cited

U.S. PATENT DOCUMENTS 4,151,195 4/1979 Warnant et al. ................ 260/465 D

FOREIGN PATENT DOCUMENTS 2843073 4/1979 Fed. Rep. of Germany .

Primary Examiner—Dolph H. Torrence
Attorney, Agent, or Firm—Burns, Doane, Swecker & Mathis

[57] ABSTRACT

Racemic modifications each consisting of specific isomers of α-cyano-3-phenoxybenzyl cis- or trans-2,2-dimethyl-3-(2,2,2-trichloroethyl)cyclopropanecarboxylate with the absolute configurations [αS, 1R] an [αR, 1S] with respect to the asymmetric carbon atoms in the alcohol and acid moieties, a method of producing the same and pesticidal compositions containing the same as active ingredient are provided. α-Cyano-3-phenoxybenzyl cis- or trans-2,2-dimethyl-3-(2,2,2-trichloroethyl)cyclopropanecarboxylate has higher pesticidal activities than those pesticides that are in general use and consequently selective production of the above specific racemic modification as defined by the combinations of the absolute configuration with respect to the asymmetric carbon atom at the position in the alcohol moiety and the absolute configuration with respect to the asymmetric carbon atom in the acid moiety provides compounds having still higher pesticidal activities.

58 Claims, No Drawings

RACEMIC MODIFICATION CONSISTING OF SPECIFIC ISOMERS OF α-CYANO-3-PHENOXYBENZYL CIS- OR TRANS-2,2-DIMETHYL-3-(2,2,2-TRICHLOROETHYL)CYCLOPROPANECARBOXYLATE, PRODUCTION THEREOF AND PESTICIDAL COMPOSITIONS CONTAINING THE SAME

This invention relates to a racemic modification consisting of specific isomers of α-cyano-3-phenoxybenzyl cis- or trans-2,2-dimethyl-3-(2,2,2-trichloroethyl)cyclopropanecarboxylate with the absolute configurations [αS, 1R] and [αR, 1S] with respect to the asymmetric carbon atoms in the alcohol and acid moieties, to a method of producing the same and to pesticidal compositions containing the same as active ingredient.

The insecticidal activity of a known synthetic pyrethroid α-cyano-3-phenoxybenzyl 2,2-dimethyl-3-(2,2-dichlorovinyl)cyclopropanecarboxylate depends for the most part on a specific isomer thereof as specified by the combination of the absolute configuration with respect to the asymmetric carbon atom in the acid moiety and the absolute configuration with respect to the asymmetric carbon atom at the α position in the alcohol moiety. There are known as such isomers having high insecticidal activities (S)-α-cyano-3-phenoxybenzyl cis-2,2-dimethyl-3-(2,2-dichlorovinyl)cyclopropane-1R-carboxylate and an oily racemic modification of α-cyano-3-phenoxybenzyl dl-trans- or cis-2,2-dimethyl-3-(2,2-dichlorovinyl)cyclopropanecarboxylate (see Japanese Patent Applications laid open under Nos. 148,040/1977 and 142,046/1977).

For the corresponding ester of 2,2-dimethyl-3-(2,2,2-trichloroethyl)cyclopropanecarboxylic acid, which is different from 2,2-dimethyl-3-(2,2-dichlorovinyl)cyclopropanecarboxylic acid, however, there has not been known the presence of a similar isomer(s) having a high pesticidal activity and consequently such an isomer has never been isolated or identified.

α-Cyano-3-phenoxybenzyl 2,2-dimethyl-3-(2,2,2-trichloroethyl)cyclopropanecarboxylate has three asymmetric carbon atoms in its molecule, as shown by the structural formula

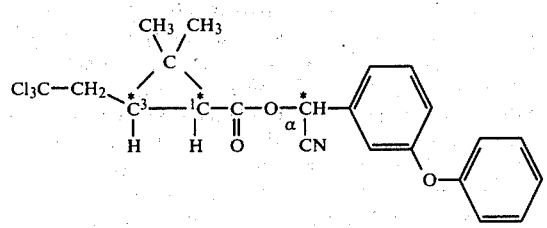

In the formula, each mark * indicates that the carbon atom to which the mark is attached is an asymmetric one. According to the findings by the present inventors, the above cyclopropanecarboxylate has high pesticidal activities against household pests and agricultural/horticultural pests but is low in toxicity to warm-blooded animals and fish. For α-cyano-3-phenoxybenzyl 2,2-dimethyl-3-(2,2,2-trichloroethyl)cyclopropanecarboxylate, there exist two geometrical isomers, namely cis and trans forms, with respect to the three-membered ring thereof, and each geometrical isomer includes the following four isomers based on the possible combinations of the absolute configurations with respect to the asymmetric carbon atoms: For the cis form:

| Acid Moiety | Alcohol moiety | | |
|---|---|---|---|
| 1R | αR | (a) | Racemic modification $D_1$ |
| 1S | αS | (b) | |
| 1R | αS | (c) | Racemic modification $D_2$ |
| 1S | αR | (d) | |

For the trans form:

| Acid Moiety | Alcohol moiety | | |
|---|---|---|---|
| 1R | αR | (a') | Racemic modification $D_1'$ |
| 1S | αS | (b') | |
| 1R | αS | (c') | Racemic modification $D_2'$ |
| 1S | αR | (d') | |

In the above representation, 1R and 1S denote the absolute configurations with respect to the position 1 in the acid moiety and αR and αS those with respect to the α position in the alcohol moiety.

For the cis form, isomer (a) and isomer (b) are optical enantiomers to each other and form a racemic modification. Similarly, isomers (c) and (d) are optical enantiomers to each other and form a racemic modification. The same may be said of isomers (a') and (b') and of isomers (c') and (d') for the trans form. Chromatography, for instance, can resolve the cis form into a racemic modification consisting of (a) and (b) (hereinafter, racemic modification $D_1$) and a racemic modification consisting of (c) and (d) (hereinafter, racemic modification $D_2$) and the trans form into a racemic modification consisting of (a') and (b') (hereinafter, racemic modification $D_1'$) and a racemic modification consisting of (c') and (d') (hereinafter, racemic modification $D_2'$). The present inventors have found that, for the cis form, racemic modification $D_2$ and, for the trans form, racemic modification $D_2'$ are much higher in pesticidal activity than racemic modification $D_1$ and racemic modification $D_1'$, respectively.

The insecticidal activities of racemic modifications $D_2$, $D_1$, $D_2'$ and $D_1'$ against the housefly are shown in Table 1.

TABLE 1

| | Activity against housefly | |
|---|---|---|
| Sample tested | LD$_{50}$ (μg/fly) | Relative activities |
| Racemic modification $D_1$ | 12.9 | 100 |
| Racemic modification $D_2$ | 0.28 | 4,600 |
| Racemic modification $D_1'$ | 1.30 | 100 |
| Racemic modification $D_2'$ | 0.35 | 370 |

The insecticidal activities were determined by the method of TEST EXAMPLE 1 to be described later. As is clear in the above table, racemic modification $D_2$ is scores of times as active as racemic modification $D_1$ and racemic modification $D_2'$ is 10 and odd times as active as racemic modification $D_1'$.

The insecticidal activities of racemic modifications $D_2$, $D_1$, $D_2'$ and $D_1'$ against the green rice leafhopper resistant to organophosphate and carbamate insecticides are shown in Table 2.

TABLE 2

| | Activity against green rice leafhopper | |
|---|---|---|
| Sample tested | LD$_{50}$ (μg/g) | Relative toxicity |
| Racemic modification $D_1$ | 128 | 100 |

TABLE 2-continued

| Sample tested | Activity against green rice leafhopper | |
|---|---|---|
| | LD$_{50}$ (μg/g) | Relative toxicity |
| Racemic modification D$_2$ | 2.35 | 5,450 |
| Racemic modification D$_1$' | 5.01 | 100 |
| Racemic modification D$_2$' | 0.41 | 1,220 |

The insecticidal activities against the green rice leafhopper were determined by the method of TEST EXAMPLE 2 described later. As is clear in the above table, racemic modification D$_2$ is scores of times as active as racemic modification D$_1$ and racemic modification D$_2$' is ten and odd times as active as racemic modification D$_1$'.

The above-mentioned racemic modification D$_2$ of α-cyano-3-phenoxybenzyl cis-2,2-dimethyl-3-(2,2,2-trichloroethyl)cyclopropanecarboxylate and racemic modification D$_2$' of α-cyano-3-phenoxybenzyl trans-2,2-dimethyl-3-(2,2,2-trichloroethyl)cyclopropanecarboxylate have excellent pesticidal activities against both susceptible and resistant strains of pests belonging to the following Orders. They are effective against the pests at all or some of their growth stages.

Order THYSANURA: e.g., *Ctenolepisma villosa Escherich;*

Order COLLEMBOLA: e.g., *Anurida trioculata Kinoshita,*
*Onychiurus pseudarmatus yaggii Miyoshi, Sminthurus viridis Linne, Bourletiella hortensis Fitch;*

Order ORTHOPTERA: e.g., Northern cone-headed long horn grasshopper (*Homorocoryphus jezoensis Matsumura* et *Shiraki*), Vegetable grosshopper (*P. sapporensis Shiraki*), Emma field cricket (*Teleogryllus emma Ohmachi et Matsuura*), Doenitz cricket (*Loxoblemmus doenitzi Stein*), Cockroach (*Blattella germanica Linné*), *Gryllotalpa africana Palisot de Beauvois, Periplaneta fuliginosa Serville;*

Order ISOPTERA: e.g., *Coptotermes formosanus Shiraki;*

Order MALLOPHAGA: e.g., *Menopon gallinae Linné, Damalinia equi Denny, Trichodectes canis De Geer;*

Order ANOPLURA: e.g. *Haematopinus eurysternus Nitzsch;*

Order THYSANOPTERA: e.g., Onion thrips (*Thrips tabaci Lindeman*), *Hercinothrips femoralis Reuter;*

Order HEMIPTERA: e.g., White-backed planthopper (*Sogatella furcifera Horváth*), Brown planthopper (*Nilaparvata lugens Stal*), Small brown planthopper (*Laodelphax striatellus Fallén*), Green rice leafhopper (*Nephotettix cincticeps Uhler*), Zigzag-striped leafhopper (*Inazuma dorsalis Motschulsky*), Black rice bug (*Scotinophara lurida Burmeister*), Rice stink bug (*Lagynotomus elongatus Dallas*), Corbett rice bug (*Leptocorixa corbetti China*), Southern green stink bug (*Nezara viridula Linné*), Grain aphid (*Rhopalosiphum padi Linné*), Japanese grain aphid (*Macrosiphum akebiae Shinji*), Corn leaf aphid (*Rhopalosiphum maidis Fitch*), Green peach aphid (*Myzus persicae Sulzer*), Cotton aphid (*Aphis gossypii Glover*), Foxglove aphid (*Aulacorthum solani Kaltenbach*), Soy bean aphid (*Aphis glycines Matsumura*), Small bean bug (*Chaulipos fallax Scott*), Bean bug (*Riptortus clavatus Thunberg*), Common green stink but (*Nezara antennata Scott*), Unibanded stink bug (*Piezodorus rubrofasciatus Fabricius*), Sloe bug (*Dolycoris baccarum Linné*), Oriental chinch bug (*Caverlerius saccharivorus Okajima*), Sugarcane cottony aphid (*Ceratovacuna lanigera Zehntner*), Cabbage aphid (*Brevicoryne brassicae Linné*), Small green plant bug (*Lygus lucorum Meyer-Dur*), Onion aphid (*Neotoxoptera formosana Takahashi*), Arrowhead scale (*Unaspis yanonensis Kuwana*), California red scale (*Aonidiella aurantii Maskell*), Viteus vitifolii Fitch, Grape leafhopper (*Erythroneura apicalis Nawa*), Grape whitefly (*Aleurolobus taonabae Kuwana*), Ume globose scale (*Eulecanium kunoense Kuwana*), Chrysanthemum aphid (*Macrosiphoniella sanborni Gillette*), Rose aphid (*Macrosiphum ibarae Matsumura*), Azalea lacewing bug (*Stephanitis pyrioides Scott*), Fern scale (*Pinnaspis aspidistrae Signoret*);

Order TRICHOPTERA: e.g. *Oecetis nigropunctata Ulmer;*

Order DIPTERA: e.g., Rice steam maggot (*Chlorops oryzae Matsumura*), Rice leaf miner (*Agromyza oryzae Munakata*), Small rice leaf miner (*Hydrellia griseola Fallén*), Paddy stem maggot (*Hydrellia sasakii Yuasa et Ishitani*), Wheat thigh chloropid fly (*Meromyza saltatrix Linné*), Leaf miner, Wheat blossom midge (*Sitodiplosis mosellana Gehin*), Soy bean root miner (*Melanagromyza dolichostigma DE Meijere*), Soy bean steam midge (*Profeltiella soya Monzen*), Soy bean stem miner (*Melanagromyza sojae Zehntner*) Soy bean pod gall midge (*Aspondylia* sp.), Seed maggot (*Hylemya platura Meigen*), Onion maggot (*Hylemya antiqua Meigen*), Stone leek leaf miner (*Phytobia cepae Hering*), Narcissus bulb fly (*Lampetia equestris Fabricius*), House fly (*Musca domestica vicina*), Mosquito (*Culex pipiens*);

Order APHANIPTERA: e.g., *Xenopsylla cheopis Rothschild, Pulex irritans Linné;*

Order HYMENOPTERA: e.g., *Dolerus hordei Rohwer,* Soy bean sawfly (*Takeuchiella pentagona Malaise*), Order LEPIDOPTERA: e.g., Rice stem borer (*Chilo suppressalis Walker*), Yellow rice borer (*Tryporyza incertulas Walker*), Pink borer (*Sesamia inferens Walker*), *Pelopidas mathias oberthuri* Evans, Grass leaf roller (*Cnaphalocrocis medinalis Guénée*), Rice leaf roller (*Susumia exigua Butler*), Rice green caterpillar (*Naranga aenescenes Moore*), Armyworm (*Leucania separata Walker*), Corn borer (*Ostrinia furvacalis Guenee*), Sweetpotato leaf folder (*Brachmia triannulella Herrich-Schaffer*), Bindweed leaf miner (*Bedellia sommulentella Zeller*), Sweetpotato leaf worm (*Aedia leucomelas Linné*), Flax budworm (*Heliothis viriplaca adaucta Butler*), Tobacco striped caterpillar (*Pyrrhia umbra Hufnagel*), Bean webworm (*Syllepte ruralis Scopli*), Soy bean pod borer (*Grapholitha glycinivorella Matsumura*), Azuki pod worm (*Matsumuraeses phaseoli Matsumura*), Lima-bean pod borer (*Etiellazinckenella Treitschke*), Oriental tobacco budworm (*Helicoverpa assulta Guenee*), Peppermint pyrausta (*Pyrausta aurata Scopoli*), Peacock butterfly, Lilac pyralid (*Margaronia nigropunctalis Bremer*), Sugarcane shoot borer (*Eucosma schistaceana Snellen*), Cabbage armyworm (*Mamestra brassicae Linné*), Tobacco cutworm (*Plodenia litura Fabricius*), Common cutworm (*Agrotis fucosa Butler*), Common cabbageworm (*Pieris rapae crucivora Boisduval*), Crucifer caterpillar (*Mesographe forficalis Linné*), Diamond-back moth (*Plutella maculipennis Curtis*), Cotton caterpillar (*Margaronia indicia Saunders*), Stone leek miner (*Acrolepia alliella Semenov et Kuznetsov*), Citrus leaf miner (*Phyllocnistis citrella Stainton*), Smaller citrus dog (*Papilio xuthus Linne*), Peach fruit moth (*Carposina niponensis Walsingham*), Oriental fruit moth (*Grapholitha molesta Busck*), Summer fruit in pesticide formulation, to prepare insecticidal compositions, which may take the form of granules, dusts, wettable powders, emulsifiable concentrates, solutions, aerosols, mosquito repellent incenses, fumigants and so on. The inert carriers include liquefied gases, liquids and solids. The liquefied gases are, for example, dichlorodifluoromethane, trichlorofluoromethane and chloroethylene, the liquid carriers are, for instance, benzene, toluene, xylene, cyclohexane, paraffin, alcohols, acetone, cyclohexanone, water and other common solvents, and examples of the solid carriers are talc, clay, kaolin, diatomaceous earth and silicates. The auxiliaries include emulsifiers, dispersants and dispersion stabilizers.

The compositions generally contain 0.01–95%, preferably 0.1–90%, by weight of racemic modification $D_2$ or $D_2'$ or mixtures of racemic modifications $D_2$ and $D_2'$ in various proportions.

Racemic modification $D_2$ or $D_2'$ or mixtures of racemic modifications $D_2$ and $D_2'$ in various proportions may be used in the form of various types of preparations such as mentioned above, and the preparations may further be modified to prepare application forms. The content of racemic modification $D_2$ or $D_2'$ or a mixture of racemic modifications $D_2$ and $D_2'$ in such application forms may vary in a very wide range. Thus the concentration of racemic modification $D_2$ or $D_2'$ or a mixture of racemic modifications $D_2$ and $D_2'$ in an application form is 0.0000001 to 100% by weight, preferably 0.0001 to 10% by weight.

The pesticidal compositions of the invention are used in a conventional manner suited for each application form.

The following SYNTHESIS EXAMPLES, TEST EXAMPLES, FORMULATION EXAMPLES and UTILITY EXAMPLES are further illustrative of the present invention, but are not by any means intended as limitative. Racemic modifications $D_2$ and $D_2'$ prepared according to the invention always had purities of not less than 90% and each contained a small amount of racemic modification $D_1$ or $D_1'$. In the FORMULATION EXAMPLES, all parts are by weight.

SYNTHESIS EXAMPLE 1

A solution of 25.9 g of 3-phenoxybenzaldehyde in 32 g of ethyl acetate was added to a solution of 11.4 g of sodium cyanide and 0.6 g of benzyltriethylammonium chloride in 49 g of water. The mixture was stirred for about 30 minutes. Then, thereto was added dropwise a solution of 45.0 g of cis-2,2-dimethyl-3-(2,2,2-trichloroethyl)cyclopropanecarbonyl chloride in 65 g of ethyl acetate at room temperature over about 3 hours, whereafter stirring was continued overnight. Then, about 200 g of water was added to the reaction mixture, the ethyl acetate layer was separated, washed with water and dried over anhydrous magnesium sulfate and the low-boiling fractions were distilled off under reduced pressure. There remained a pale yellow oil which was α-cyano-3-phenoxybenzyl cis-2,2-dimethyl-3-(2,2,2-trichloroethyl)cyclopropanecarboxylate and a mixture of racemic modification $D_1$ and racemic modification $D_2$ in a ratio of 51/49 [determined by high performance liquid chromatography using a Waters Associates' μ-Porasil column and a mixed solvent consisting of diethyl ether and n-hexane (4/96)]. Preparative liquid chromatography using a Waters Associates' Prep LC/System 500, Prep PAK— TM 500/SILICA column and a mixed solvent consisting of diethyl ether and n-hexane (4/96) gave racemic modification $D_1$ as the first main fraction and racemic modification $D_2$ as the second main fraction. The so separated and purified mixtures amounted to 51.3 g in all (86% based on the 3-phenoxybenzaldehyde).

The racemic modifications $D_1$ and $D_2$ respectively had the following characteristics.

Racemic modification $D_1$: NMR spectrum (90 MHz) $\delta_{HMS}^{CDCl_3}$: 1.18, 1.20 (each s) 6H; 1.38–1.75 (m) 2H; 2.73–3.20 (m) 2H; 6.28 (s) 1H; 6.88–7.43 (m) 9H Racemic modification $D_2$: Melting point: 59°–60° C. (recrystallized from isopropanol);
NMR spectrum (90 MHz) $\delta_{HMS}^{CDCl_3}$:
1.15, 1.17 (each s) 6H; 1.46–1.78 (m) 2H;
2.77–3.28 (m) 2H; 6.30 (s) 1H; 6.90–7.47 (m) 9H

SYNTHESIS EXAMPLE 2

Potassium tert-butoxide (0.03 g) was added to a solution of 1.00 g of racemic modification $D_1$ of α-cyano-3-phenoxybenzyl cis-2,2-dimethyl-3-(2,2,2-trichloroethyl)cyclopropanecarboxylate in 1.5 ml of isopropanol. The mixture was stirred for a day at room temperature with occasional addition of very small amounts of crystals of racemic modification $D_2$ as seed crystals. After further stirring at 5° C. for a day, the resulting crystals were collected by filtration and washed with cold petroleum ether. The so-obtained crystals of racemic modification $D_2$ of the α-cyano-3-phenoxybenzyl cis-2,2-dimethyl-3-(2,2,2-trichloroethyl)cyclopropanecarboxylate weighed 0.60 g. The characteristic properties of the racemic modification $D_2$ were in good agreement with those of the racemic modification $D_2$ prepared in SYNTHESIS EXAMPLE 1.

A mixture of racemic modification $D_1$ and racemic modification $D_2$ was recovered as a residue from the mother liquor after the separation of the above-mentioned racemic modification $D_2$ by removing low-boiling fractions from said mother liquor under reduced pressure.

SYNTHESIS EXAMPLES 3–10

200 mg of racemic modification $D_1$ or a mixture of racemic modification $D_1$ and racemic modification $D_2$ of α-cyano-3-phenoxybenzyl cis-2,2-dimethyl-3-(2,2,2-trichloroethyl)cyclopropanecarboxylate was dissolved in a solvent in which racemic modification $D_1$ was soluble but racemic modification $D_2$ was insoluble. Then, a basic agent was added and the mixture was stirred with occasional addition of very small amounts of crystals of racemic modification $D_2$ as seed crystals at room temperature and then at 5° C. There separated out crystals. Thereafter, following the procedure of SYNTHESIS EXAMPLE 2, crystals of racemic modification $D_2$ were obtained. The results obtained under various conditions are summarized in Table 2.

TABLE 2

| Example | $D_1/D_2$ ratio in starting material | Basic agent (mg) | Solvent (mg) | Reaction temperature and time | Yield of racemic modification $D_2$ (mg) |
|---|---|---|---|---|---|
| 3 | 10/0 | n-Butylamine | Isopropanol | Room temp.  24 hrs | 110 |

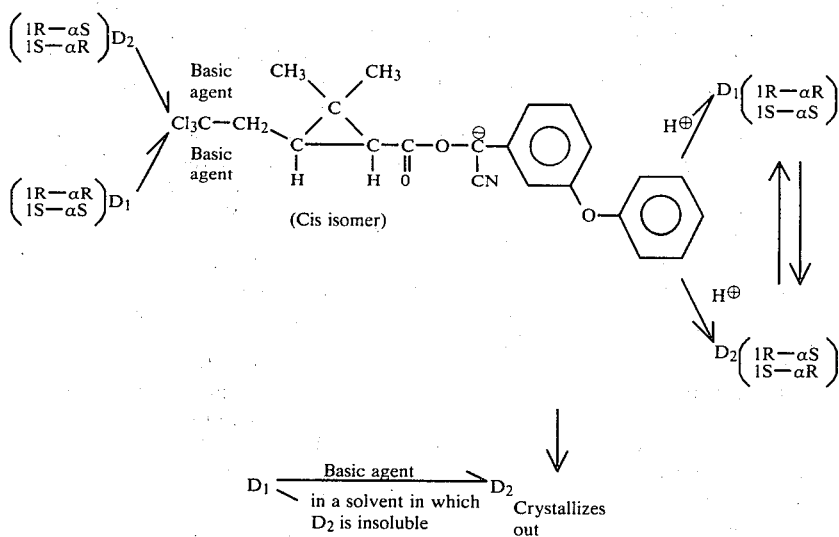

Thus, under the action of the basic agent, racemic modification $D_1$ yields an α-cyanocarbanion, which then undergoes protonation and gives racemic modification $D_2$ and racemic modification $D_1$. Since isomerization of racemic modification $D_2$ into racemic modification $D_1$ can occur as well in the solution comprising racemic modification $D_1$, racemic modification $D_2$ and the solvent in the presence of the basic agent, racemic modification $D_1$ and racemic modification $D_2$ are in an equilibrium state in that solution. When racemic modification $D_1$ is soluble in the solvent used but racemic modification $D_2$ is insoluble in it, the equilibrium shifts in a manner such that racemic modification $D_2$ is formed in response to crystallization of racemic modification $D_2$ out of the reaction system and as a result crystals of racemic modification $D_2$ are obtained in a good yield.

The above-mentioned α-cyano-3-phenoxybenzyl cis- or trans-2,2-dimethyl-3-(2,2,2-trichloroethyl)cyclopropanecarboxylate can be prepared either by method (i) or by method (ii) shown below.

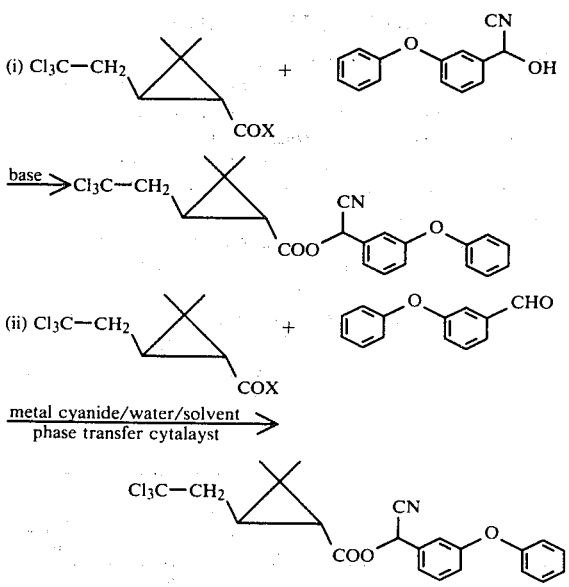

-continued
(in the formulas, X = halogen)

Thus, in method (i), cis- or trans-2,2-dimethyl-3-(2,2,2-trichloroethyl)cyclopropanecarbonyl halide or a mixture of these is condensed with α-cyano-3-phenoxybenzyl alcohol in the presence of base such as tertiary amine, e.g. triethyl amine, pyridine; alkali metal carbonate, e.g. sodium carbonate, potassium carbonate; or alkali bicarbonate, e.g. sodium hydrogen carbonate. In method (ii), cis- or trans-2,2-dimethyl-3-(2,2,2-trichloroethyl)cyclopropanecarbonyl halide or a mixture of these, 3-phenoxybenzaldehyde and a metal cyanide such as sodium cyanide or potassium cyanide are reacted in a solvent such as toluene, ethyl acetate, carbon tetrachloride, diisopropyl ether or methylene chloride and preferably in the presence of water, if necessary in the presence of a phase transfer catalyst such as tricyclohexylethylphosphonium chloride, dibenzo-18-crown-6, benzyltriethylammonium chloride or tetrabutylammonium chloride. The α-cyano-3-phenoxybenzyl cis- or trans-2,2-dimethyl-3-(2,2,2-trichloroethyl)cyclopropanecarboxylate or a mixture of these thus obtained by method (i) or method (ii) is a mixture in which the ratio of racemic modifications $D_1/D_2$ or $D_1'/D_2'$ is from about 50/50 to about 58/42.

Racemic modification $D_2$ or $D_2'$ with high pesticidal activities can be isolated from the mixture of racemic modification $D_1$ and racemic modification $D_2$ or the mixture of racemic modification $D_1'$ and racemic modification $D_2'$ or the mixture of these as prepared by the above method (i) or (ii) by chromatography or crystallization. The remaining racemic modification $D_1$ or $D_1'$ with lower pesticidal activities as well as the mixture of racemic modifications $D_1$ and $D_2$ or the mixture of racemic modifications $D_1'$ and $D_2'$ or the mixture of these as prepared by the above-mentioned method can be submitted to the isomerization according to the invention, to produce the desired racemic modification $D_2$ or $D_2'$.

Racemic modification $D_2$ or $D_2'$ or mixtures of racemic modifications $D_2$ and $D_2'$ in various proportions can be used with inert carriers, with or without addition of auxiliaries in accordance with the practice common racemic modification $D_2'$ proceeds until an equilibrium composition is finally reached in that solvent. The resulting mixture is resolved into racemic modification $D_1$ and racemic modification $D_2$ or into racemic modification $D_1'$ and racemic modification $D_2'$ by chromatography or selective crystallization. The pesticidally less active racemic modification $D_1$ or $D_1'$ or a mixture (of racemic modifications $D_1$ and $D_2$ and/or $D_1'$ and $D_2'$) containing a major amount of such racemic modification $D_1$ or $D_1'$ after the resolution can repeatedly be subjected to the isomerization according to the invention, if necessary after addition of an appropriate amount of the starting material thereto. The amount of the solvent is not critical but preferably is 1–10 times as much as the starting material on the weight basis. The isomerization can be carried out at any temperature at which decomposition of the starting material is insignificant. The higher the temperature is, the more rapidly the isomerization proceeds. Generally, the isomerization is conducted at a temperature within the range of from $-50°$ C. to the boiling point of the solvent employed. Conveniently, the isomerization is conducted at a temperature obtainable by ice cooling to room temperature. The time required for the isomerization depends upon the reaction temperature as well as the amount and basicity of the basic agent used. Generally, desirable results can be obtained by the reaction for several hours to 3 days.

On the other hand, in case racemic modification $D_1$ is soluble in the solvent used but racemic modification $D_2$ is insoluble in it, racemic modification $D_2$ continuously separates out as crystals from the reaction system with the progress of the isomerization of racemic modification $D_1$ into racemic modification $D_2$. Therefore, the crystals of racemic modification $D_2$ can easily be collected by using such a technique as decantation, filtration or centrifugation after completion of the isomerization reaction. Similarly, in case racemic modification $D_1'$ is soluble in the solvent used but racemic modification $D_2'$ is insoluble in it, racemic modification $D_2'$ continuously crystallizes out of the reaction system with the progress of the isomerization reaction and the resulting crystals of racemic modification $D_2'$ can easily be recovered by the same technique as the one mentioned above for the case of isolation of racemic modification $D_2$. Seeding the reaction mixture with a small amount of relatively pure crystals of racemic modification $D_2$ or $D_2'$ may facilitate crystallization of racemic modification $D_2$ or $D_2'$ from the reaction mixture, although such seeding is not always necessary. In the liquid phase remaining after the separation of racemic modification $D_2$ or $D_2'$, there coexist at equilibrium racemic modifications $D_1$ and $D_2$ or racemic modifications $D_1'$ and $D_2'$. The liquid phase can repeatedly be subjected to the isomerization according to the present invention after concentrating the liquid phase, if necessary followed by addition of a fresh portion of the basic agent, or after adding to the liquid phase a fresh portion of the starting material and, if necessary, a fresh portion of the basic agent. Those solvents in which racemic modification $D_1$ or $D_1'$ is soluble but racemic modification $D_2$ or $D_2'$ is insoluble can easily be anticipated and selected from the above-mentioned solvents by measuring the solubility each of racemic modifications $D_1$ and $D_2$ or racemic modifications $D_1'$ and $D_2'$ at a temperature attainable under ice cooling to room temperature. It should be noted that "soluble" and "insoluble" have been used herein as relative terms. Selection of the solvent should preferably be made such that the difference between the solubility of racemic modification $D_1$ and that of racemic modification $D_2$ or between the solubility of racemic modification $D_1'$ and that of racemic modification $D_2'$ is as great as possible, or in other words, such that racemic modification $D_2$ or $D_2'$ can crystallize more easily than racemic modification $D_1$ or $D_1'$. Examples of preferred solvents are alkanols such as methanol, ethanol, isopropanol, n-propanol and normal and branched-chain butanols or pentanols; mixtures of an alkanol and an aliphatic hydrocarbon such as petroleum ether, pentane, hexane or heptane; acetonitrile; mixtures of acetonitrile and water; aliphatic hydrocarbons such as pentane and hexane; aliphatic hydrocarbons each containing a small amount of an aromatic hydrocarbon such as benzene or toluene; ethers such as diisopropyl ether; and so forth. Considering the yields attainable, such alkanols as isopropanol, n-butanol and tert-butanol are especially preferred. It is necessary that the amount of the solvent should be less than the amount thereof which just gives a saturated solution of the starting material at the temperature at which the isomerization is to be actually performed on the supposition that the starting material consists wholly of racemic modification $D_2$ or $D_2'$. Preferably, the amount of the solvent is 0.5–8 parts, more preferably 1–4 parts, by weight per part by weight of the starting material. The isomerization temperature is required to be lower than the melting point of racemic modification $D_2$ or $D_2'$, and generally it is in the range from $-50°$ C. to about $40°$ C., preferably from $-15°$ C. to room temperature. The time required for the isomerization reaction depends upon the reaction temperature as well as the amount and basicity of the basic agent used. Generally, several hours to 3 days of reaction can give satisfactory results.

The isomerization of racemic modification $D_1$ into racemic modification $D_2$ according to the invention presumably takes place in conformity with the mechanism shown in the following. The mechanism of the isomerization of racemic modification $D_1'$ into racemic modification $D_2'$ is considered to be similar.

tortrix (*Adoxophyes orana Fischer von Roslerstamm*), Gypsy moth (*Lymantria dispar Linné*), Tent caterpillar (*Malacosoma neustria testacea Motschulsky*), Small grape plume moth (*Stenoptilia vitis Sasaki*), Persimmon fruit moth (*Stathmopoda flavofasciata Nagano*), Fall webworm (*Hyphantria cunea Drury*), Japanese lawn grass cutworm (*Rusidrina depravata Butler*), Pectinophora gossypiella;

Order COLEOPTERA: e.g., Rice leaf beetle (*Oulema oryzae Kuwayama*), Large 28-spotted lady beetle (*Henosepilachna vigintioctomaculata Motshulsky*), 28-spotted lady beetle (*H. vigintioctopunctata Fabricius*), False melon beetle (*Atrachya menetriesi Faldermann*), Two-striped leaf beetle (*Paraluperodes nigrobilineatus Motschulsky*), Bean leaf beetle (*Colposcelis signata Motschulky*), Bean frosted weevil (*Eugnathus distinctus Roelofs*), Castaneous garden beetle (*Maladera castanea Arrow*), Soy bean beetle (*Anomala rufocuprea Motschulsky*), Bean blister beetle (*Epicauta gorhami Marseul*), Peppermint leaf beetle (*Chrysolina exanthematica Wiedemann*), Olive engraved weevil (*Hylobius cribripennis Matsumura et Kono*), Vegetable weevil (*Listroderes obliquus Klug*), Cucurbit leaf beetle (*Aulacophora femoralis Motschulsky*), Boll weevil (*Anthonomus grandis Boh.*), Rice weevil (*Sitophilus zeamais Motschulsky*), Lesser grain borer (*Rhizopertha dominica Fabricius*), Azuki bean weevil (*Callosobruchus chinensis Linne*), Mustard beetle (*Phaedon cochleariae Fab.*), Boll weevil;

Order ACARINA: e.g., Winter grain mite *Penthaleus major Duges*), Two-spotted spider mite (*Tetranychus urticae Koch*), Carmine mite (*Tetranychus telarius Linne*); and so forth.

In addition, racemic modifications $D_2$ and $D_2'$ are expected to be repellent to mites and ticks and also to show synergism with other biologically active compounds. Therefore, they can be used widely as agents for controlling agricultural, horticultural and forest pests, pests to stored grain, household pests, and/or mites and ticks.

Furthermore, as a result of intensive investigations as to isomerization of those pesticidally less active racemic modifications $D_1$ and $D_1'$ into those pesticidally more active racemic modifications $D_2$ and $D_2'$, respectively, the present inventors have found that racemic modifications $D_1$ and $D_1'$ can easily be isomerized into racemic modifications $D_2$ and $D_2'$, respectively, by reacting a basic agent with racemic modifications $D_1$ and $D_1'$, without causing any significant side reactions such as ester bond cleavage. This finding also had led to the present invention.

Thus, the invention also provides a method of isomerizing racemic modifications $D_1$ and $D_1'$ into racemic modifications $D_2$ and $D_2'$, respectively, which comprises bringing the starting material, namely racemic modification $D_1$ or a mixture (hereinafter, mixture M) of racemic modification $D_1$ and racemic modification $D_2$ wherein the amount of racemic modification $D_2$ is less than the amount thereof to be found after equilibration of $D_1/D_2$ isomerization, or racemic modification $D_1'$ or a mixture (hereinafter, mixture M') of racemic modification $D_1'$ and $D_2'$ wherein the amount of racemic modification $D_2'$ is less than the amount thereof to be found after equilibration of $D_1'/D_2'$ isomerization, or a mixture of two or more of these, into contact with a basic agent in the presence or absence of a solvent.

The basic agent to be used in the isomerization according to the invention includes aliphatic amines such as n-propylamine, n-butylamine, sec-butylamine, tert-butylamine, n-pentylamine, cyclohexylamine, benzylamine, diethylamine, diisopropylamine, di-n-butylamine, piperidine, pyrrolidine, trimethylamine, triethylamine, tri-n-butylamine, 1,8-diazabicyclo[5,4,0]-7-undecene (DBU), 1,5-diazabicyclo[4,3,0]-5-nonene (DBN), tetramethylenediamine, ethanolamine and morpholine; aromatic amines such as aniline and 1-naphthylamine; quaternary ammonium bases such as tetramethylammonium hydroxide and tetraethylammonium hydroxide; phosphorus bases such as triphenylphosphine, alkali and alkaline earth metal hydroxides such as sodium hydroxide, potassium hydroxide, barium hydroxide and calcium hydroxide; alkali and alkaline earth metal carbonates and bicarbonates such as sodium carbonate, potassium carbonate, sodium hydrogen carbonate and calcium carbonate; alkali metal alcoholates such as sodium methoxide, sodium isopropoxide and potassium tert-butoxide; alkali and alkaline earth metal salts of weak organic acids such as sodium acetate and magnesium formate; basic ion exchange resins; high molecular weight liquid amines, ammonia; and alkali metal cyanides such as potassium cyanide. Among these basic agents, preferred are aliphatic amines, alkali or alkaline earth metal hydroxides, alkali or alkaline earth metal carbonates or bicarbonates and alkali metal alcoholates. Aliphatic amines are especially preferred. The basic agent may be used in an amount of 0.01-400 mole %, preferably 1-150 mole %, based on the starting material.

Desirably, the isomerization according to the invention is carried out in a solvent. Examples of the solvents are ketones such as acetone, methyl ethyl ketone and cyclohexanone, aromatic hydrocarbons such as benzene and toluene, ethers such as diethyl ether, diisopropyl ether, dibutyl ether, tetrahydrofuran and dioxane, nitriles such as acetonitrile and propionitrile, halogenated hydrocarbons such as chloroform, methylene chloride, carbon tetrachloride, 1,1,1-trichloroethane, hexachloroethane, tetrachloroethylene and chlorobenzene, esters such as ethyl acetate and isobutyl acetate, alkanols such as methanol, ethanol, n-propanol, isopropanol, n-butanol, sec-butanol, tert-butanol, 3-methyl-1-butanol, n-pentanol, n-hexanol, octanol and ethylene glycol, aliphatic hydrocarbons such as petroleum ether, pentane, hexane and cyclohexane, dimethyl sulfoxide, N,N-dimethylformamide, N,N-dimethylacetamide, water and mixture of these.

In case racemic modification $D_1$ and racemic modification $D_2$ are both soluble in the solvent used, the isomerization of racemic modification $D_1$ into racemic modification $D_2$ proceeds until an equilibrium is reached with respect to the isomerization reaction, giving a mixture of almost equal amounts of racemic modification $D_1$ and racemic modification $D_2$, although the composition of the resulting mixture may vary to some extent depending upon the kind of the solvent used. In case racemic modification $D_1'$ is isomerized into racemic modification $D_2'$ in a solvent in which racemic modification $D_1'$ and racemic modification $D_2'$ are both soluble, too, there is obtained a mixture of racemic modification $D_1'$ and racemic modification $D_2'$ with a composition corresponding to isomerization equilibrium. Therefore, when a basic agent acts on racemic modification $D_1$, mixture M, racemic modification $D_1'$ or mixture M' or a mixture of two or more of these, the isomerization of racemic modification $D_1$ into racemic modification $D_2$ or of racemic modification $D_1'$ into

TABLE 2-continued

| Example | D₁/D₂ ratio in starting material | Basic agent (mg) | Solvent (mg) | Reaction temperature and time | | Yield of racemic modification D₂ (mg) |
|---|---|---|---|---|---|---|
|   |   | 10 | 250 | 5° C. | 24 hrs |   |
| 4 | " | n-Butylamine 10 | n-Propanol 300 | Room temp. 5° C. | 8 hrs 12 hrs | 60 |
| 5 | " | n-Butylamine 12 | n-Butanol 300 | Room temp. 5° C. | 8 hrs 12 hrs | 75 |
| 6 | " | n-Butylamine 17 | Isopropanol 200 Diisopropyl ether 50 | Room temp. 5° C. | 8 hrs 12 hrs | 100 |
| 7 | 80/20 | Aqueous ammonia (NH₃ 25%) 45 | Isopropanol 280 | Room temp. 5° C. | 48 hrs 12 hrs | 127 |
| 8 | " | Diisopropylamine 10 | Isopropanol 250 | Room temp. 5° C. | 24 hrs 12 hrs | 95 |
| 9 | " | Piperdine 18 | Isopropanol 250 | Room temp. 5° C. | 12 hrs 48 hrs | 130 |
| 10 | " | n-Butylamine 14 | Ethanol 250 | Room temp. 5° C. | 12 hrs 48 hrs | 16 |

SYNTHESIS EXAMPLE 11

Following the procedure of SYNTHESIS EXAMPLE 1 except that toluene was used in place of the ethyl acetate used in SYNTHESIS EXAMPLE 1, there was obtained a crude product as an oil. The crude product was purified by preparative liquid chromatography to give 50.5 g (83% yield) of α-cyano-3-phenoxybenzyl cis-2,2-dimethyl-3-(2,2,2-trichloroethyl)cyclopropanecarboxylate. The ratio of racemic modifications D₁/D₂ was 58/42.

1.00 g of the so-prepared cyclopropanecarboxylate was dissolved in 1.5 ml of isopropanol, 0.069 g of n-butylamine was then added, and the mixture was stirred at room temperature overnight. A very small amount of crystals of racemic modification D₂ as seed crystals was added and stirring was continued at 5° C. for 8 hours. Crystals separated out and were collected by filtration and washed with cold petroleum ether to give 0.45 g of racemic modification D₂ of α-cyano-3-phenoxybenzyl cis-2,2-dimethyl-3-(2,2,2-trichloroethyl)cyclopropanecarboxylate as crystals. The filtrate was concentrated to about 1 g by distilling off low boiling fractions. The residue was stirred at 5° C. for a day to give 0.28 g of crystals of racemic modification D₂. About 200 mg of a mixture of racemic modification D₁ and racemic modification D₂ was recovered by distilling off low-boiling fractions under reduced pressure from the filtrate after separation of the second crop.

SYNTHESIS EXAMPLE 12

To a solution of 10.0 g of cis-2,2-dimethyl-3-(2,2,2-trichloroethyl)cyclopropanecarbonyl chloride in 80 ml of dry benzene, there were added first 8.5 g of α-cyano-3-phenoxybenzyl alcohol and then gradually 4.5 g of pyridine. The mixture was stirred at room temperature overnight. About 70 ml of water was added to the reaction mixture, the benzene layer was separated, washed with water and dried over anhydrous magnesium sulfate, and low-boiling fractions were distilled off under reduced pressure. The oily product thus obtained was purified by preparative liquid chromatography following the procedure of SYNTHESIS EXAMPLE 1 to give 12.1 g (70% yield) of α-cyano-3-phenoxybenzyl cis-2,2-dimethyl-3-(2,2,2-trichloroethyl)cyclopropanecarboxylate with a ratio of racemic modifications D₁/D₂ of about 50/50.

1.00 g of the so-obtained cyclopropanecarboxylate was dissolved in 1.5 ml of isopropanol, then 0.060 g of n-butylamine was added, and, following the procedure of SYNTHESIS EXAMPLE 11, there was obtained 0.75 g of crystals of racemic modification D₂ of α-cyano-3-phenoxybenzyl cis-2,2-dimethyl-3-(2,2,2-trichloroethyl)cyclopropanecarboxylate. About 200 mg of a mixture of racemic modification D₁ and racemic modification D₂ was recovered from the filtrate.

SYNTHESIS EXAMPLE 13

To a solution of 200 mg of racemic modification D₁ of α-cyano-3-phenoxybenzyl cis-2,2-dimethyl-3-(2,2,2-trichloroethyl)cyclopropanecarboxylate in 250 mg of n-hexane, there was added 12 mg of n-butylamine, and the mixture was stirred at room temperature for a day with occasional addition of very small amounts of crystals of racemic modification D₂ as seed crystals. Stirring was then continued at 5° C. overnight. Thereafter, 150 mg of n-hexane and a very small amount of crystals of racemic modification D₂ were added and the resulting mixture was stirred at 5° C. for 4 days. Crystals precipitated. Following the procedure of SYNTHESIS EXAMPLE 2, there was obtained 80 mg of racemic modification D₂.

SYNTHESIS EXAMPLES 14–24

200 mg of the racemic modification D₁ separated and purified in SYNTHESIS EXAMPLE 1, was dissolved in each of various solvents specified in Table 3. A specified amount of a basic agent was added and the mixture was stirred at room temperature for 2 days. The reaction mixture was analyzed by high performance liquid chromatography under the same conditions as those metioned in SYNTHESIS EXAMPLE 1 for the ratio of racemic modifications D₁/D₂. The results are summarized in Table 3.

TABLE 3

| Example | Solvent (mg) | Basic agent (mg) | ratio of racemic modifications D₁/D₂ in solution |
|---|---|---|---|
| 14 | tert-Butanol 250 | Potassium tert-butoxide 13 | 56/44 |

TABLE 3-continued

| Example | Solvent (mg) | Basic agent (mg) | ratio of racemic modifications $D_1/D_2$ in solution |
|---|---|---|---|
| 15 | Acetonitrile 250 | Potassium tert-butoxide 13 | 50/50 |
| 16 | Isopropanol 300 | Triethylamine 18 | 53/47 |
| 17 | Isopropanol 250 | DBU 4 | 52/48 |
| 18 | Diisopropyl ether 250 | n-Butylamine 12 | 54/46 |
| 19 | Diisopropyl ether 250 | Potassium tert-butoxide 5 | 55/45 |
| 20 | Benzene 200 | Piperidine 16 | 54/46 |
| 21 | N,N-Dimethylformamide 200 | n-Butylamine 12 | 50/50 |
| 22 | Dimethyl sulfoxide 200 | Morpholine 23 | 50/50 |
| 23 | 1,1,1-Trichloroethane 200 | Pyrrolidine 17 | 52/48 |
| 24 | Ethyl acetate 200 | Triethylamine 12 | 53/47 |

SYNTHESIS EXAMPLE 25

A solution of 25.9 g of 3-phenoxybenzaldehyde in 32 g of ethyl acetate was added to a solution of 11.4 g of sodium cyanide and 0.6 g of benzyltriethylammonium chloride in 49 g of water, and the mixture was stirred for about 30 minutes. A solution of 45.0 g of trans-2,2-dimethyl-3-(2,2,2-trichloroethyl)cyclopropanecarbonyl chloride in 65 g of ethyl acetate was added dropwise to the mixture at room temperature over about 3 hours, whereafter stirring was continued overnight. About 200 g of water was added to the reaction mixture, the ethyl acetate layer was separated, washed with water and dried over anhydrous magnesium sulfate and low-boiling fractions were distilled off under reduced pressure. There was obtained as a pale yellow oil a 51/49 mixture of racemic modification $D_1'$ and racemic modification $D_2'$ of α-cyano-3-phenoxybenzyl trans-2,2-dimethyl-3-(2,2,2-trichloroethyl)cyclopropanecarboxylate. [The $D_1'/D_2'$ ratio was determined by high performance liquid chromatography using a Waters Associates' μ-Porasil column and a mixed solvent consisting of diethyl ether and n-hexane (4/96).] The mixture was subjected to preparative liquid chromatography using a Waters Associates' Prep LC/System 500, Prep PA-K—TM 500/SILICA column and a mixed solvent consisting of diethyl ether and n-hexane (4/96) and there were obtained racemic modification $D_1'$ as the first main fraction and racemic modification $D_2'$ as the second main fraction. The racemic modifications so separated and purified totaled to 55.0 g (93% yield based on the 3-phenoxybenzaldehyde).

The characteristics of the racemic modifications $D_1'$ and $D_2'$ were as follows:

Racemic modification $D_1'$: NMR spectrum (90 MHz) $\delta_{HMS}^{CDCl_3}$ 1.15, 1.25 (each s) 6H; 1.46(d)1H; 1.76(q)1H; 2.52(dd), 2.80(dd)2H; 6.33(s)1H; 6.85–7.38(m)9H Racemic modification $D_2'$: Melting point: 101.5°–102° C. (recrystallized from isopropanol); NMR spectrum (90 MHz) $\delta_{HMS}^{CDCl_3}$: 1.13, 1.16(each s)6H; 1.47(d)1H; 1.83(q)1H; 2.63(dd), 2.84(dd)2H; 6.36(s)1H; 6.89–7.44 (m)9H

SYNTHESIS EXAMPLE 26

Triethylamine (0.223 g) was added to a solution of 1.00 g of racemic modification $D_1'$ of α-cyano-3-phenoxybenzyl trans-2,2-dimethyl-3-(2,2,2-trichloroethyl)cyclopropanecarboxylate in 1.5 ml of isopropanol and the mixture was stirred at room temperature. Crystals precipitated. They were collected by filtration and washed with n-hexane to give 0.88 g of racemic modification $D_2'$ of α-cyano-3-phenoxybenzyl trans-2,2-dimethyl-3-(2,2,2-trichloroethyl)cyclopropanecarboxylate. The characteristics of the so obtained racemic modification $D_2'$ were identical to those of the racemic modification $D_2'$ prepared in SYNTHESIS EXAMPLE 25.

A mixture of racemic modification $D_1'$ and racemic modification $D_2'$ was recovered as a residue from the mother liquor after the collection of the above racemic modification $D_2'$ by removing low-boiling fractions from said mother by reduced pressure distillation.

SYNTHESIS EXAMPLES 27–40

1.00 g of racemic modification $D_1'$ or of a mixture of racemic modification $D_1'$ and racemic modification $D_2'$ of α-cyano-3-phenoxybenzyl trans2,2-dimethyl-3-(2,2,2-trichloroethyl)cyclopropanecarboxylate was reacted with a basic agent at room temperature in a solvent in which racemic modification $D_1'$ was soluble but racemic modification $D_2'$ was insoluble and, following the procedure of SYNTHESIS EXAMPLE 26, racemic modification $D_2'$ was collected. The results obtained under various conditions are summarized in Table 4.

TABLE 4

| Example | Ratio of racemic modifications $D_2'/D_2'$ | Basic agent | (g) | Solvent (ml) | | Reaction time (hrs) | Yield (g) of racemic modification $D_2'$ |
|---|---|---|---|---|---|---|---|
| 27 | 10/0 | Sodium hydroxide | 0.010 | Isopropanol | 2.0 | 24 | 0.71 |
| 28 | ″ | Potassium tert-butoxide | 0.020 | ″ | | ″ | 0.82 |
| 29 | ″ | Aqueous ammonia (NH₃ 25%) | 0.108 | Acetonitrile Water | 1.5 0.5 | ″ | 0.83 |
| 30 | ″ | Aqueous ammonia (NH₃ 25%) | ″ | tert-Butanol | 1.5 | ″ | 0.79 |
| 31 | ″ | Benzylamine | 0.200 | Isopropanol | 2.0 | ″ | 0.62 |
| 32 | ″ | Triethylamine | 0.160 | n-Hexane Isopropanol | 1.5 0.5 | 27 | 0.46 |
| 33 | ″ | ″ | 0.160 | n-Hexane | 1.0 | 48 | 0.32 |

TABLE 4-continued

| Example | Ratio of racemic modifications $D_2'/D_2'$ | Basic agent | (g) | Solvent (ml) | | Reaction time (hrs) | Yield (g) of racemic modification $D_2'$ |
|---|---|---|---|---|---|---|---|
| 34 | " | " | 0.460 | Benzene<br>n-Hexane | 80 mg<br>2.0 | 27 | 0.40 |
| 35 | 80/20 | n-Butylamine | 0.132 | Isopropanol | 2.0 | 20 | 0.60 |
| 36 | " | Piperidine | 0.153 | " | " | " | 0.68 |
| 37 | " | Aqueous ammonia (NH₃ 25%) | 0.108 | " | " | " | 0.67 |
| 38 | " | Triethylamine | 0.077 | " | 1.5 | 37 | 0.82 |
| 39 | " | " | 0.138 | " | " | " | 0.84 |
| 40 | 50/50 | " | 0.223 | " | " | " | 0.89 |

SYNTHESIS EXAMPLE 41

The procedure of SYNTHESIS EXAMPLE 25 was followed except that toluene was used in place of the ethyl acetate used in SYNTHESIS EXAMPLE 25. There was obtained a crude oily product, which was purified by preparative liquid chromatography to give 52.7 g (89% yield) of α-cyano-3-phenoxybenzyl trans-2,2-dimethyl-3-(2,2,2-trichloroethyl)cyclopropanecarboxylate with a ratio of racemic modifications $D_1'/D_2'$ of 58/42.

10.00 g of the so prepared cyclopropanecarboxylate was dissolved in 20 ml of isopropanol, 1.53 g of piperidine was then added, and the mixture was stirred at room temperature for a day. Crystals separated out. They were collected by filtration and washed with n-hexane to give 8.10 g of racemic modification $D_2'$ of α-cyano-3-phenoxybenzyl trans-2,2-dimethyl-3-(2,2,2-trichloroethyl)cyclopropanecarboxylate.

SYNTHESIS EXAMPLE 42

α-Cyano-3-phenoxybenzyl alcohol (8.5 g) was added to a solution of 10.0 g of trans-2,2-dimethyl-3-(2,2,2-trichloroethyl)cyclopropanecarbonyl chloride in 80 ml of dry benzene, then 4.5 g of pyridine was added gradually and the mixture was stirred at room temperature overnight. Thereafter, about 70 ml of water was added to the reaction mixture, the benzene layer was separated, washed with water and dried over anhydrous magnesium sulfate, and low-boiling fractions were distilled off under reduced pressure. There was obtained an oily product, which was purified by preparative liquid chromatography under the conditions mentioned in SYNTHESIS EXAMPLE 25 to give 13.3 g (77% yield) of α-cyano-3-phenoxybenzyl trans-2,2-dimethyl-3-(2,2,2-trichloroethyl)cyclopropanecarboxylate with a ratio of racemic modifications $D_1'/D_2'$ of about 50/50.

The cyclopropanecarboxylate (13.3 g) was dissolved in 25 ml of isopropanol, 1.80 g of triethylamine was added, and the mixture was stirred at room temperature for a day. Crystals separated out. They were filtered off and washed with n-hexane to give 10.9 g of racemic modification $D_2'$ of α-cyano-3-phenoxybenzyl trans-2,2-dimethyl-3-(2,2,2-trichloroethyl)cyclopropanecarboxylate.

TEST EXAMPLE 1

Mortality test with houseflies by topical application method

The test samples, namely racemic modification $D_1$, racemic modification $D_2$, racemic modification $D_1'$ and racemic modification $D_2'$, were each accurately weighed and dissolved in acetone at predetermined concentrations. Female adult houseflies were anesthetized with ether and 1 μl of each acetone solution was micropipetted onto the prothoracicodorsal region of each housefly. 30 houseflies were used for each concentration. The houseflies, together with feed, were placed in a tall dish and kept at a temperature of 25° C. with a wire gauze placed on the dish. After 24 hours, the houseflies were examined for deaths, the mortalities were calculated and then the $LD_{50}$ value (50% lethal dose) was then determined. The results were as shown previously in Table 1.

TEST EXAMPLE 2

Mortality test with green rice leafhoppers by topical application method

The test samples, namely racemic modification $D_1$, racemic modification $D_2$, racemic modification $D_1'$ and racemic modification $D_2'$, were each accurately weighed and dissolved in acetone at predetermined concentrations. Female adult green rice leafhoppers resistant to organophosphorus and carbamate insecticides were anesthetized with carbon dioxide gas, and 0.5 μl of each solution was micropipetted onto the thoracicoabdominal region of each leafhopper. The test leafhoppers, in groups of 15, were then kept at 25° C. with access to rice plant seedlings. After 24 hours, the leafhoppers were examined for deaths, the mortalities were calculated and the $LD_{50}$ (50% lethal dose) value was then determined. The results were as shown previously in Table 2.

FORMULATION EXAMPLE 1

0.2 part of each of racemic modification $D_2$ and racemic modification $D_2'$ was added to a sufficient amount of kerosene to make 100 parts. The mixture was stirred to obtain an oil preparation of each racemic modification.

FORMULATION EXAMPLE 2

A 30% emulsifiable concentrate of each of racemic modification $D_2$ and racemic modification $D_2'$ was prepared by adding 50 parts of xylene and 20 parts of a surfactant SORPOL SM-200 (SORPOL is a trademark of Toho Kagaku Gokyo K. K.) to 30 parts of each racemic modification and stirring the resulting mixture.

FORMULATION EXAMPLE 3

A wettable powder of each of racemic modification $D_2$ and racemic modification $D_2'$ was prepared by adding 5 parts of a surfactant SORPOL SM-200 (Toho Kagaku Gokyo K. K.) to 20 parts of each racemic modification, followed by through mixing, adding 75 parts of talc and thoroughly stirring the resulting mixture in a triturator.

FORMULATION EXAMPLE 4

A 0.2% dust of each of racemic modification $D_2$ and racemic modification $D_2'$ was prepared by dissolving 0.2 part of each racemic modification in 20 parts of acetone, adding 99.8 parts of clay, adequately stirring the resulting mixture, evaporating the acetone and thoroughly stirring the residual mixture in a triturator.

FORMULATION EXAMPLE 5

A 0.3% dust was prepared by dissolving 0.3 part of each of racemic modification $D_2$ and racemic modification $D_2'$ in 20 parts of acetone, adding 99.7 parts of clay, adequately stirring the resulting mixture, evaporating the acetone and thoroughly stirring the residual mixture in a triturator.

UTILITY EXAMPLE 1

The 0.3% dust of racemic modification $D_2$ prepared in FORMULATION EXAMPLE 5 and the 0.2% dust of racemic modification $D_2'$ prepared in FORMULATION EXAMPLE 4 were respectively dusted over rice plant seedlings in an amount of 5 kg per are by using a bell jar duster. Then 30 individuals of the organophosphorus- and carbamate-resistant green rice leafhopper were released. After 24 hours, the leafhoppers were examined for deaths. The mortality was more than 90% for each of the dusts.

UTILITY EXAMPLE 2

The 30% emulsifiable concentrate of racemic modification $D_2$ prepared in FORMULATION EXAMPLE 2 was diluted with water so that the concentration of racemic modification $D_2$ was 50 ppm. The dilution was sprayed over a soya bean seedling and then 10 third-instar larvae of the tobacco cutworm were released. In 24 hours, all of the tobacco cutworms were killed. In a control test, a 50 ppm dilution of racemic modification $D_1$ prepared in the same manner could not kill any tobacco cutworm at all.

What is claimed is:

1. A composition of matter selected from the group consisting of, racemic modification $D_2$, (S)-α-cyano-3-phenoxybenzyl (cis, 1R)-2,2-dimethyl-3-(2,2,2-trichloroethyl) cyclopropanecarboxylate and (R)-α-cyano-3-phenoxybenzyl (cis, 1S)-2,2-dimethyl-3-(2,2,2-trichloroethyl) cyclopropanecarboxylate, and, racemic modification $D_2'$, (S)-α-cyano-3-phenoxybenzyl (trans, 1R)-2,2-dimethyl-3-(2,2,2-trichloroethyl) cyclopropanecarboxylate and (R)-α-cyano-3-phenoxybenzyl (trans, 1S)-2,2-dimethyl-3-(2,2,2-trichloroethyl) cyclopropanecarboxylate, and admixtures thereof.

2. The composition of matter as defined by claim 1, wherein said composition is racemic modification $D_2$, (S)-α-cyano-3-phenoxybenzyl (cis, 1R)-2,2-dimethyl-3-(2,2,2-trichloroethyl) cyclopropanecarboxylate and (R)-α-cyano-3-phenoxybenzyl (cis, 1S)-2,2-dimethyl-3-(2,2,2-trichloroethyl) cyclopropanecarboxylate.

3. The composition of matter as defined in claim 1, wherein said composition is racemic modification $D_2'$, (S)-α-cyano-3-phenoxybenzyl (trans, 1R)-2,2-dimethyl-3-(2,2,2-trichloroethyl) cyclopropanecarboxylate and (R)-α-cyano-3-phenoxybenzyl (trans, 1S)-2,2-dimethyl-3-(2,2,2-trichloroethyl) cyclopropanecarboxylate.

4. A method for producing a racemic modification consisting of (R)-α-cyano-3-phenoxybenzyl (cis, 1S)-2,2-dimethyl-3-(2,2,2-trichloroethyl) cyclopropanecarboxylate and (S)-α-cyano-3-phenoxybenzyl (cis, 1R)-2,2-dimethyl-3-(2,2,2-trichloroethyl) cyclopropanecarboxylate (racemic modification $D_2$) and/or racemic modification consisting of (R)-α-cyano-3-phenoxybenzyl (trans, 1S)-2,2-dimethyl-3-(2,2,2-trichloroethyl) cyclopropanecarboxylate and (S)-α-cyano-3-phenoxybenzyl (trans, 1R)-2,2-dimethyl-3-(2,2,2-trichloroethyl) cyclopropanecarboxylate (racemic modification $D_2'$) which comprises isomerizing a racemic modification consisting of (R)-α-cyano-3-phenoxybenzyl (cis, 1R)-2,2-dimethyl-3-(2,2,2-trichloroethyl) cyclopropanecarboxylate and (S)-α-cyano-3-phenoxybenzyl (cis, 1S)-2,2-dimethyl-3-(2,2,2-trichloroethyl) cyclopropanecarboxylate (racemic modification $D_1$) and/or a racemic modification consisting of (R)-α-cyano-3-phenoxybenzyl (trans, 1R)-2,2-dimethyl-3-(2,2,2-trichloroethyl) cyclopropanecarboxylate and (S)-α-cyano-3-phenoxybenzyl (trans, 1S)-2,2-dimethyl-3-(2,2,2-trichloroethyl) cyclopropanecarboxylate (racemic modification $D_1'$) by contacting racemic modification $D_1$, an admixture of racemic modification $D_1$ and racemic modification $D_2$ wherein the amount of racemic modification $D_2$ in said admixture is less than that existing upon equilibration of the $D_1/D_2$ isomerization, racemic modification $D_1'$, an admixture of racemic modification $D_1'$ and racemic modification $D_2'$ wherein the amount of racemic modification $D_2'$ in said admixture is less than that existing upon equilibration of the $D_1'/D_2'$ isomerization, or a mixture of two or more of these with a basic reagent in the presence or absence of a solvent.

5. The method as defined by claim 4, said basic reagent being selected from the group consisting of aliphatic amines, aromatic amines, quaternary ammonium bases, basic phosphorus compounds, alkali metal hydroxides, alkaline earth metal hydroxides, alkali metal carbonates, alkali metal hydrogen carbonates, alkaline earth metal carbonates, alkali metal alcoholates, alkali and alkaline earth metal salts of weak organic acids, basic ion exchange resins, high molecular weight liquid amines, ammonia and alkali metal cyanides.

6. The method as defined by claim 5, said basic reagent being selected from the group consisting of aliphatic amines, alkali and alkaline earth metal hydroxides, alkali and alkaline earth metal carbonates, alkali metal hydrogen carbonates and alkali metal alcoholates.

7. The method as defined by claim 6, said basic reagent being an aliphatic amine.

8. The method as defined by claim 4, said isomerization being carried out in the presence of a solvent.

9. The method as defined by claim 8, wherein racemic modifications $D_1$ and $D_2$ and/or racemic modifications $D_1'$ and $D_2'$ are soluble in the solvent.

10. The method as defined by claim 8, wherein racemic modification $D_1$ is soluble in the solvent and racemic modification $D_2$ is insoluble therein, and/or racemic modification $D_1'$ is soluble in the solvent and racemic modification $D_2'$ is insoluble therein.

11. The method for producing racemic modification $D_2$ as defined by claim 4, wherein racemic modification $D_1$ is isomerized by contacting racemic modification $D_1$ or an admixture of racemic modification $D_1$ and racemic modification $D_2$ wherein the amount of racemic modification $D_2$ in said admixture is less than that existing upon equilibration of $D_1/D_2$ isomerization with a basic reagent in the presence of a solvent in which racemic modification $D_1$ is soluble in the solvent and racemic modification $D_2$ is insoluble therein.

12. The method for producing racemic modification $D_2'$ as defined by claim 4, wherein racemic modification $D_1'$ is isomerized by contacting racemic modification $D_1'$ or an admixture of racemic modification $D_1'$ and racemic modification $D_2'$ wherein the amount of racemic modification $D_2'$ in said admixture is less than that existing upon equilibration of $D_1'/D_2'$ isomerization with a basic reagent in the presence of a solvent in which racemic modification $D_1'$ is soluble in the solvent and racemic modification $D_2'$ is insoluble therein.

13. The method as defined by claim 8, said solvent being selected from the group consisting of an alkanol, mixtures of alkanol and an aliphatic hydrocarbon, acetonitrile, mixtures of acetonitrile and water, an aliphatic hydrocarbon, an aliphatic hydrocarbon containing a minor amount of an aromatic hydrocarbon and an ether.

14. The method as defined by claim 13, said solvent being an alkanol.

15. The method as defined by claim 14, said solvent being isopropanol.

16. The method as defined by claim 14, said solvent being tert-butanol.

17. The method as defined by claim 8, wherein 0.5 to 8 parts by weight of solvent is used per one part by weight of the starting material, namely racemic modification $D_1$, an admixture of racemic modification $D_1$ and racemic modification $D_2$ wherein the amount of racemic modification $D_2$ in said admixture is less than that existing upon equilibration of $D_1/D_2$ isomerization, racemic modification $D_1'$, an admixture of racemic modification $D_1'$ and racemic modification $D_2'$ wherein the amount of racemic modification $D_2'$ in said admixture is less than that existing upon equilibration of $D_1'/D_2'$ isomerization, or a mixture of two or more of these.

18. The method as defined by claim 17, wherein 1 to 4 parts by weight of solvent is used per one part by weight of the starting material.

19. The method as defined in claim 10, the temperature of isomerization ranging from $-50°$ C. to $40°$ C.

20. The method as defined by claim 19, the temperature of isomerization ranging from $-15°$ C. to room temperature.

21. A method for producing a racemic modification consisting of (R)-α-cyano-3-phenoxybenzyl (cis, 1S)-2,2-dimethyl-3-(2,2,2-trichloroethyl) cyclopropanecarboxylate and (S)-α-cyano-3-phenoxybenzyl (cis, 1R)-2,2-dimethyl-3-(2,2,2-trichloroethyl) cyclopropanecarboxylate (racemic modification $D_2$) and/or racemic modification consisting of (R)-α-cyano-3-phenoxybenzyl (trans, 1S)-2,2-dimethyl-3-(2,2,2-trichloroethyl) cyclopropanecarboxylate and (S)-α-cyano-3-phenoxybenzyl (trans, 1R)-2,2-dimethyl-3-(2,2,2-trichloroethyl) cyclopropanecarboxylate (racemic modification $D_2'$) which comprises (A) isomerizing racemic modification consisting of (R)-α-cyano-3-phenoxybenzyl (cis, 1R)-2,2-dimethyl-3-(2,2,2-trichloroethyl) cyclopropanecarboxylate and (S)-α-cyano-3-phenoxybenzyl (cis, 1S)-2,2-dimethyl-3-(2,2,2-trichloroethyl) cyclopropanecarboxylate (racemic modification $D_1$) and/or racemic modification consisting of (R)-α-cyano-3-phenoxybenzyl (trans, 1R)-2,2-dimethyl-3-(2,2,2-trichloroethyl) cyclopropanecarboxylate and (S)-α-cyano-3-phenoxybenzyl (trans, 1S)-2,2-dimethyl-3-(2,2,2-trichloroethyl) cyclopropanecarboxylate (racemic modification $D_1'$) by contacting an admixture of racemic modifications $D_1$ and $D_2$ and/or an admixture of racemic modifications $D_1'$ with a basic reagent in the presence of a solvent in which racemic modification $D_1$ is soluble in the solvent and racemic modification $D_2$ is insoluble therein and/or in which racemic modification $D_1'$ is soluble in the solvent and racemic modification $D_2'$ is insoluble therein, and separating said racemic modification $D_2$ and/or racemic modification $D_2'$ as crystals from the reaction system upon progress of the isomerization reaction, or (B) separating racemic modification $D_2$ and/or racemic modification $D_2'$ from an admixture of racemic modification $D_1$ and $D_2$ and/or an admixture of racemic modifications $D_1'$ and $D_2'$ by a physical means, and (B-1) isomerizing the residual racemic modification $D_1$ and/or racemic modification $D_1'$ by contacting said residual racemic modification(s) with a basic reagent in the presence of a solvent in which racemic modification $D_1$ is soluble in said solvent and racemic modification $D_2$ is insoluble therein and/or in which racemic modification $D_1'$ is soluble in said solvent and racemic modification $D_2'$ is insoluble therein, and separating said racemic modification $D_2$ and/or racemic modification $D_2'$ as crystals from the reaction system upon progress of the isomerization reaction, or (B-2) isomerizing the residual racemic modification $D_1$ and/or racemic modification $D_1'$ by contacting said residual racemic modification(s) with a basic reagent in the presence of a solvent in which racemic modifications $D_1$ and $D_2$ and/or racemic modifications $D_1'$ and $D_2'$ are soluble to obtain an admixture of racemic modifications $D_1$ and $D_2$ and/or an admixture of racemic modifications $D_1'$ and $D_2'$, and separating racemic modification $D_2$ and/or racemic modification $D_2'$ from the above obtained admixture of racemic modifications $D_1$ and $D_2$ and/or admixture of racemic modifications $D_1'$ and $D_2'$ by a physical means.

22. The method as defined by claim 21, said basic reagent being selected from the group consisting of aliphatic amines, aromatic amines, quaternary ammonium bases, basic phosphorus compounds, alkali metal hydroxides, alkaline earth metal hydroxides, alkali metal carbonates, alkali metal hydrogen carbonates, alkaline earth metal carbonates, alkali metal alcoholates, alkali and alkaline earth metal salts of weak organic acids, basic ion exchange resins, high molecular weight liquid amines, ammonia and alkali metal cyanides.

23. The method as defined by claim 22, said basic reagent being selected from the group consisting of aliphatic amines, alkali and alkaline earth metal hydroxides, alkali and alkaline earth metal carbonates, alkali metal hydrogen carbonates and alkali metal alcoholates.

24. The method as defined by claim 23, said basic reagent being an aliphatic amine.

25. The method as defined by claim 21, wherein the solvent in which racemic modification $D_1$ is soluble in the solvent and racemic modification $D_2$ is insoluble therein and/or in which racemic modification $D_1'$ is soluble in the solvent and racemic modification $D_2'$ is insoluble therein is selected from the group consisting of an alkanol, mixtures of alkanol and an aliphatic hydrocarbon, acetonitrile, mixtures of acetonitrile and water, an aliphatic hydrocarbon, an aliphatic hydrocarbon containing a minor amount of an aromatic hydrocarbon and an ether.

26. The method as defined by claim 25, said solvent being an alkanol.

27. The method as defined by claim 26, said solvent being isopropanol.

28. The method as defined by claim 26, said solvent being tert-butanol.

29. A method for producing a racemic modification consisting of (R)-α-cyano-3-phenoxybenzyl (cis, 1S)-2,2-dimethyl-3-(2,2,2-trichloroethyl) cyclopropanecarboxylate and (S)-α-cyano-3-phenoxybenzyl (cis, 1R)-2,2-dimethyl-3-(2,2,2-trichloroethyl) cyclopropanecarboxylate (racemic modification $D_2$) and/or racemic modification consisting of (R)-α-cyano-3-phenoxybenzyl (trans, 1S)-2,2-dimethyl-3-(2,2,2-trichloroethyl) cyclopropanecarboxylate and (S)-α-cyano-3-phenoxybenzyl (trans, 1R)-2,2-dimethyl-3-(2,2,2-trichloroethyl) cyclopropanecarboxylate (racemic modification $D_2'$) which comprises (I) obtaining an admixture of racemic modification $D_2$ and racemic modification consisting of (R)-α-cyano-3-phenoxybenzyl (cis, 1R)-2,2-dimethyl-3-(2,2,2-trichloroethyl) cyclopropanecarboxylate and (S)-α-cyano-3-phenoxybenzyl (cis, 1S)-2,2-dimethyl-3-(2,2,2-trichloroethyl) cyclopropanecarboxylate (racemic modification $D_1$) and/or an admixture of racemic modification $D_2'$ and racemic modification consisting of (R)-α-cyano-3-phenoxybenzyl (trans, 1R)-2,2-dimethyl-3-(2,2,2-trichloroethyl) cyclopropanecarboxylate and (S)-α-cyano-3-phenoxybenzyl (trans, 1S)-2,2-dimethyl-3-(2,2,2-trichloroethyl) cyclopropanecarboxylate (racemic modification $D_1'$) by (i) reacting cis- or trans-2,2-dimethyl-3-(2,2,2-trichloroethyl) cyclopropanecarbonyl halide or a mixture of these with 3-phenoxybenzaldehyde in the presence of a metal cyanide or (ii) reacting cis- or trans-2,2-dimethyl-3-(2,2,2-trichloroethyl) cyclopropanecarbonyl halide or a mixture of these with α-cyano-3-phenoxybenzyl alcohol in the presence of base and (II) (A) isomerizing racemic modification $D_1$ and/or racemic modification $D_1'$ by contacting the above obtained admixture of racemic modifications $D_1$ and $D_2$ and/or admixture of racemic modifications $D_1'$ and $D_2'$ with a basic reagent in the presence of a solvent in which racemic modification $D_1$ is soluble in the solvent and racemic modification $D_2$ is insoluble therein and/or in which racemic modification $D_1'$ is soluble in the solvent and racemic modification $D_2'$ is insoluble therein, and separating said racemic modification $D_2$ and/or racemic modification $D_2'$ as crystals from the reaction system upon progress of the isomerization reaction, or (B) separating racemic modification $D_2$ and/or racemic modification $D_2'$ from the above obtained admixture of racemic modifications $D_1$ and $D_2$ and/or admixture of racemic modifications $D_1'$ and $D_2'$ by a physical means, and (B-1) isomerizing the residual racemic modification $D_1$ and/or racemic modification $D_1'$ by contacting said residual racemic modification(s) with a basic reagent in the presence of a solvent in which racemic modification $D_1$ is soluble in the solvent and racemic modification $D_2$ is insoluble therein and/or in which racemic modification $D_1'$ is soluble in the solvent and racemic modification $D_2'$ is insoluble therein, and separating said racemic modification $D_2$ and/or racemic modification $D_2'$ as crystals from the reaction system upon progress of the isomerization reaction, or (B-2) isomerizing the residual racemic modification $D_1$ and/or racemic modification $D_1'$ by contacting said residual racemic modification(s) with a basic reagent in the presence of a solvent in which racemic modifications $D_1$ and $D_2$ and/or racemic modifications $D_1'$ and $D_2'$ are soluble to obtain an admixture of racemic modifications $D_1$ and $D_2$ and/or an admixture of racemic modifications $D_1'$ and $D_2'$, and separating racemic modification $D_2$ and/or racemic modification $D_2'$ from the above obtained admixture of racemic modifications $D_1$ and $D_2$ and/or admixture of racemic modifications $D_1'$ and $D_2'$ by a physical means.

30. The method as defined by claim 29, said basic reagent being selected from the group consisting of aliphatic amines, aromatic amines, quaternary ammonium bases, basic phosphorus compounds, alkali metal hydroxides, alkaline earth metal hydroxides, alkali metal carbonates, alkali metal hydrogen carbonates, alkaline earth metal carbonates, alkali metal alcoholates, alkali and alkaline earth metal salts of weak organic acids, basic ion exchange resins, high molecular weight liquid amines, ammonia and alkali metal cyanides.

31. The method as defined by claim 30, said basic reagent being selected from the group consisting of aliphatic amines, alkali and alkaline earth metal hydroxides, alkali and alkaline earth metal carbonates, alkali metal hydrogen carbonates and alkali metal alcoholates.

32. The method as defined by claim 32 said basic reagent being an aliphatic amine.

33. The method as defined by claim 29, wherein the solvent in which racemic modification $D_1$ is soluble in the solvent and racemic modification $D_2$ is insoluble therein and/or in which racemic modification $D_1'$ is soluble in the solvent and racemic modification $D_2'$ is insoluble therein is selected from the group consisting of an alkanol, mixtures of alkanol and an aliphatic hydrocarbon, acetonitrile, mixtures of acetonitrile and water, an aliphatic hydrocarbon, an aliphatic hydrocarbon containing a minor amount of an aromatic hydrocarbon and an ether.

34. The method as defined by claim 33, said solvent being an alkanol.

35. The method as defined by claim 34, said solvent being isopropanol.

36. The method as defined by claim 34, said solvent being tert-butanol.

37. A pesticidal composition of matter, comprising a pesticidally effective amount of, racemic modification $D_2$, (S)-α-cyano-3-phenoxybenzyl (cis, 1R)-2,2-dimethyl-3-(2,2,2-trichloroethyl) cyclopropanecarboxylate and (R)-α-cyano-3-phenoxybenzyl (cis, 1S)-2,2-dimethyl-3-(2,2,2-trichloroethyl) cyclopropanecarboxylate, or racemic modification $D_2'$, (S)-α-cyano-3-phenoxybenzyl (trans, 1R)-2,2-dimethyl-3-(2,2,2-trichloroethyl) cyclopropanecarboxylate and (R)-α-cyano-3-phenoxybenzyl (trans, 1S)-2,2-dimethyl-3-(2,2,2-trichloroethyl) cyclopropanecarboxylate, or admixtures thereof, and a pesticidally effective carrier material therefor.

38. The pesticidal composition of matter as defined by claim 37, comprising a pesticidally effective amount of racemic modification $D_2$, (S)-α-cyano-3-phenoxybenzyl (cis, 1R)-2,2-dimethyl-3-(2,2,2-trichloroethyl) cyclopropanecarboxylate and (R)-α-cyano-3-phenoxybenzyl (cis, 1S)-2,2-dimethyl-3-(2,2,2-trichloroethyl) cyclopropanecarboxylate.

39. The pesticidal composition of matter as defined by claim 37, comprising a pesticidally effective amount of racemic modification $D_2'$, (S)-α-cyano-3-phenoxybenzyl (trans, 1R)-2,2-dimethyl-3-(2,2,2-trichloroethyl) cyclopropanecarboxylate and (R)-α-cyano-3-phenoxybenzyl (trans, 1S)-2,2-dimethyl-3-(2,2,2-trichloroethyl) cyclopropanecarboxylate.

40. The pesticidal composition of matter as defined by claim 37, comprising from 0.01 to 95% by weight of racemic modification $D_2$, racemic modification $D_2'$ or admixture thereof.

41. The pesticidal composition of matter as defined by claim 40 comprising from 0.1 to 90% by weight of racemic modification D₂, racemic modification D₂' or admixtures thereof.

42. The pesticidal composition of matter as defined by claim 37, formulated in granular form.

43. The pesticidal composition of matter as defined by claim 37, formulated in dust form.

44. The pesticidal composition of matter as defined by claim 37, formulated in wettable powder form.

45. The pesticidal composition of matter as defined by claim 37, formulated in emulsifiable concentrate form.

46. The pesticidal composition of matter as defined by claim 37, formulated in liquid solution form.

47. The pesticidal composition of matter as defined by claim 37, formulated in aerosol form.

48. The pesticidal composition of matter as defined by claim 37, formulated in incense form.

49. The pesticidal composition of matter as defined by claim 37, formulated in fumigant form.

50. The pesticidal composition of matter as defined by claim 37, said pesticidally effective carrier material being an inert member selected from the group consisting of liquified gas, liquid and solid.

51. A method for the control of pests, comprising applying to the habitat of such pests, a pesticidally effective amount of, racemic modification $D_2$, (S)-α-cyano-3-phenoxybenzyl (cis, 1R)-2,2-dimethyl-3-(2,2,2-trichloroethyl) cyclopropanecarboxylate and (R)-α-cyano-3-phenoxybenzyl (cis, 1S)-2,2-dimethyl-3-(2,2,2-trichloroethyl) cyclopropanecarboxylate, or racemic modification $D_2'$, (S)-α-cyano-3-phenoxybenzyl (trans, 1R)-2,2-dimethyl-3-(2,2,2-trichloroethyl) cyclopropanecarboxylate and (R)-α-cyano-3-phenoxybenzyl (trans, 1S)-2,2-dimethyl-3-(2,2,2-trichloroethyl) cyclopropanecarboxylate, or admixtures thereof.

52. The method as defined by claim 51, comprising applying to the habitat of such pests, a pesticidally effective amount of racemic modification $D_2$, (S)-α-cyano-3-phenoxybenzyl (cis, 1R)-2,2-dimethyl-3-(2,2,2-trichloroethyl) cyclopropane-carboxylate and (R)-α-cyano-3-phenoxybenzyl (cis, 1S)-2,2-dimethyl-3-(2,2,2-trichloroethyl) cyclopropanecarboxylate.

53. The method as defined by claim 51, comprising applying to the habitat of such pests, a pesticidally effective amount of racemic modification $D_2'$, (S)-α-cyano-3-phenoxybenzyl (trans, 1R)-2,2-dimethyl-3-(2,2,2-trichloroethyl) cyclopropanecarboxylate and (R)-α-cyano-3-phenoxybenzyl (trans, 1S)-2,2-dimethyl-3-(2,2,2-trichloroethyl) cyclopropanecarboxylate.

54. The method as defined by claim 51, said pesticidally effective amount being applied in a concentration of from 0.0000001 to 100% by weight.

55. The method as defined by claim 54, said concentration being from 0.0001 to 10% by weight.

56. The method as defined by claim 51, said habitat being that of a pest selected from the group consisting of agricultural pest, horticultural pest, forest pest, stored grain pest, household pest, mite and tick.

57. The method as defined by claim 51, said habitat being that of a pest selected from the group consisting of Thysanura, Collembola, Orthoptera, Isoptera, Mallophaga, Anoplura, Thysanoptera, Hemiptera, Trichoptera, Diptera, Aphaniptera, Hymenoptera, Lepidoptera, Coleoptera and Acarina.

58. The method as defined by claim 51, said habitat being a rice paddy field.

* * * * *